United States Patent [19]
Peery et al.

[11] Patent Number: 5,821,096
[45] Date of Patent: Oct. 13, 1998

[54] **PEPTIDOGLYCAN BIOSYNTHETIC GENE MURE FROM *STREPTOCOCCUS PNEUMONIAE***

[75] Inventors: Robert Brown Peery, Brownsburg; Paul Luther Skatrud, Indianapolis, both of Ind.

[73] Assignee: Eli Lilly and Company, Indianapolis, Ind.

[21] Appl. No.: 818,857

[22] Filed: Mar. 17, 1997

Related U.S. Application Data

[62] Division of Ser. No. 655,114, May 29, 1996, Pat. No. 5,712,108.

[51] Int. Cl.$^6$ .............................. C12N 9/00; C12N 1/20; C12N 15/00; C07H 21/04
[52] U.S. Cl. .................. 435/183; 435/252.3; 435/320.1; 435/325; 536/23.2; 935/22; 935/66
[58] Field of Search ........................ 536/23.2; 435/183, 435/320.1, 325, 252.3; 935/22, 66

[56] References Cited

U.S. PATENT DOCUMENTS 5,712,108  1/1998  Peery et al. .................. 435/15

OTHER PUBLICATIONS

Daniel, Richard A., et al., J. of General Microbiology, 139:361–370 (1993).
Michaud, Catherine, et al., Eur. J. Biochem., 194: 853–861 (1990).
Tao, Jing–Song, et al., Can. J. Microbiol., 35, 1051–1054 (1989).
Jacobs, M.R. (1992) Treatment and Diagnosis of Infections Caused by Drug–Resistant *Streptococcus Pheumoniae*, Clin. Infect. Dis. 15: 119–127.
Flouret, B., et al., (1981) Reverse–Phase High–Pressure Liquid Chromatography of Uridine Dipohosphate N–Acetylmuramyl Peptide Precursors of Bacterial Cell Wall Peptidoglycan, Anal. Biochem. 114: 59–63.

*Primary Examiner*—Robert A. Wax
*Assistant Examiner*—Einar Stole
*Attorney, Agent, or Firm*—Thomas D. Webster; David E. Boone

[57] ABSTRACT

The invention provides isolated nucleic acid compounds encoding the murE stem peptide biosynthetic gene of *Streptococcus pneuinoniae*. Also provided are vectors and transformed heterologous host cells for expressing the murE enzyme product and a method for identifying compounds that inhibit stem peptide biosynthesis.

9 Claims, 1 Drawing Sheet

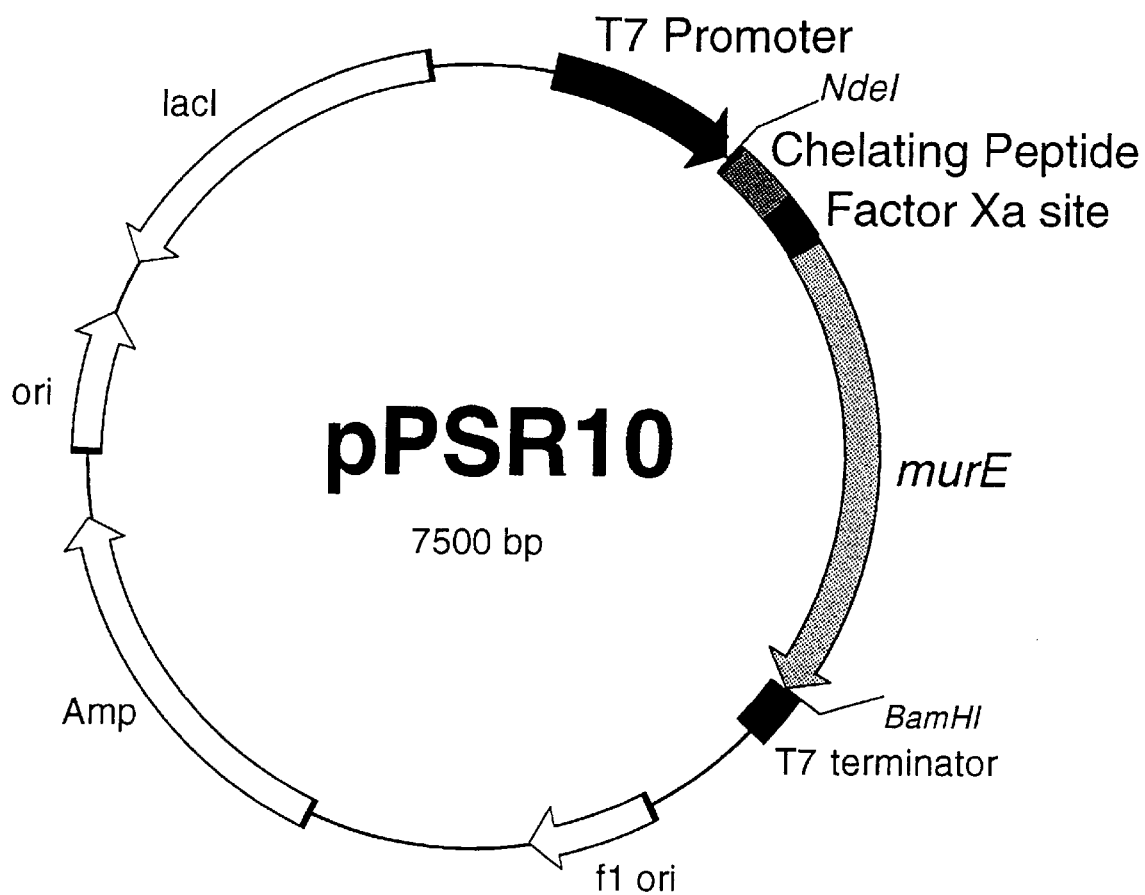

PEPTIDOGLYCAN BIOSYNTHETIC GENE MURE FROM *STREPTOCOCCUS PNEUMONIAE*

This application is a division of U.S. application Ser. No. 08/655,114, filed May 29, 1996, which issued on Jan. 27, 1998, as U.S. Pat. No. 5,712,108.

BACKGROUND OF THE INVENTION

This invention relates to recombinant DNA technology. In particular the invention pertains to the cloning of the murE gene encoding uridine-diphosphate-N-acetylmuramoyl-L-alanyl-D-glutamate:L-lysine ligase of *Streptococcus pneunoniae* and the use of the murE gene and the encoded protein in a screen for new inhibitors of bacterial cell wall biosynthesis.

The emergence of antibiotic resistance in common pathogenic bacterial species has justifiably alarmed the medical and research communities. Frequently these organisms are co-resistant to several different antibacterial agents. Pathogens resistant to frequently utilized antibiotics are found in the clinical as well as the community setting. Particularly problematic in the community setting has been the emergence and rapid spread of beta-lactam resistance in *Streptococcus pneumoniae* which frequently causes upper respiratory tract infections. Resistance to beta-lactams in this organism is due to modification of one or more of the penicillin-binding proteins (PBP's) which are involved in cell wall biosynthesis and are the targets for beta-lactam antibiotics.

Interference with bacterial cell wall biosynthesis is an especially attractive antibacterial target because an analogous structure does not exist in mammalian cells so that many such compounds have low toxicity in humans and potentially high therapeutic value.

The bacterial cell wall structure comprises a peptidoglycan layer which provides mechanical rigidity for the bacterium. This segment of the cell wall is composed of a sugar backbone (alternating residues of N-acetylglucosamine and N-acetylmuramic acid) attached to a pentapeptide (also referred to as "stem peptide," or "Park nucleotide") containing alternating D and L amino acid residues. The nascent peptidoglycan layer is stabilized by an enzymatic step which crosslinks adjacent pentapeptide moieties. Without this crosslinking step the peptidoglycan structure is severely weakened and susceptible to degradation. Indeed, it is this crosslinking step that has been a frequently targeted site for antibiotic compounds such as the beta-lactam antibiotics.

In contrast to the beta-lactam case, which targets the crosslinking step, the pathway involved in the synthesis of the stem peptide has not been widely exploited as a target for inhibitory compounds. The stem peptide biosynthetic pathway comprises at least 10 steps in which the stem peptide is added onto UDPMurNAc by the stepwise addition of amino acid residues. In the first step, catalyzed by the UDPGlcNAc enolpyruvyl transferase and NADH-dependent reductase, UDPGlcNAc is converted to UDPMurNAc. In five subsequent steps, catalyzed by N-acetylmuramate:L-alanine ligase; UDP-N-acetyl-muramoyl-L-alanine:D-glutamate ligase; UDP-N-acetyl-muramoyl-L-alanyl-D-glutamate:lysine ligase; UDP-N-acetylmuramoyl-L-alanyl-D-glutamyl-L-lysine:D-alanyl-D-alanine ligase; and D-alanyl-D-alanine synthetase, the final product, UDPMurNAc-L-Ala-D-Glu-L-lysine-D-Ala-D-Ala, is produced in *Streptococcus pneumoniae*.

The enzymatic steps involved in the formation of the stem peptide are potentially a rich source for new antibacterial targets. A few inhibitors, which target this pathway, have been developed. For example, D-cycloserine, inhibits the alanine racemase and the D-alanine-D-alanine synthetase; phosphonomycin inhibits UDP-GlcNac conversion to UDP-GlcNac-enolpyruvate; and Ala-phosphonine inhibits the addition of L-Alanine in the formation of UDP-MurNac-L-Ala.

The genes directly involved with assembly of the stem peptide in *Escherichia coli* have been cloned and characterized. These genes occur in two clusters on the *E. coli* chromosome. Analogous genes have been cloned from *Bacillus subtilus,* and from *Haemophilus influenzae* (Fleischmann et al., Science, 269:496–512 (1996)).

While inroads in the development of new antibiotics and new targets for antibiotic compounds have been made with a variety of microorganisms, progress has been less apparent in *Streptococcus pneumoniae*. In part, *Streptococcus pneumoniae* presents a special case because the organism is highly mutagenic and readily takes up exogenous DNA from its surroundings. Thus, the need for new antibacterial compounds and new targets for antibacterial therapy is especially acute in *Streptococcus pneumoniae*.

SUMMARY OF THE INVENTION

The present invention is designed to meet the aforementioned need and provides, inter alia, isolated nucleic acid molecules that encode the murE gene product from *Streptococcus pneumoniae*. The invention also provides the protein product of the *Streptococcus pneumoniae* murE gene, uridine-diphosphate-N-acetyulmuramoyl-L-alanyl-D-glutamate:L-lysine ligase (MurE protein), in substantially purified form.

Having the cloned murE gene of *Streptococcus pneumoniae* enables the production of large quantities of the cognate enzyme from which large scale screens can be developed to identify new antibacterial compounds targeted at the stem peptide biosynthetic pathway. It may be possible to combine several of the proteins involved in stem peptide biosynthesis in a single screen to examine several steps at the same time. The key proteins may be structurally analyzed such that structure-based drug design may be used to develop novel compounds effective in the treatment of antibiotic resistant mircroorganisms.

In one embodiment the present invention is a DNA molecule comprising the nucleotide sequence identified as SEQ ID NO. 1:

| ATG | ATT | AAG | ATT | GAA | ACC | GTA | TTA | GAT | ATT | TTA | AAG | AAA | GAT | GGC | CTT | 48 |
|---|---|---|---|---|---|---|---|---|---|---|---|---|---|---|---|---|
| Met | Ile | Lys | Ile | Glu | Thr | Val | Leu | Asp | Ile | Leu | Lys | Lys | Asp | Gly | Leu | |
| 1 | | | | 5 | | | | | 10 | | | | | 15 | | |

| TTT | CGC | GAA | ATT | ATT | GAC | CAA | GGT | CAT | TAC | CAC | TAC | AAC | TAC | AGC | AAA | 96 |
|---|---|---|---|---|---|---|---|---|---|---|---|---|---|---|---|---|
| Phe | Arg | Glu | Ile | Ile | Asp | Gln | Gly | His | Tyr | His | Tyr | Asn | Tyr | Ser | Lys | |
| | | | | 20 | | | | | 25 | | | | | 30 | | |

| | | | | | | | | | | | | | | | |
|---|---|---|---|---|---|---|---|---|---|---|---|---|---|---|---|
| GTT | ATT | TTT | GAT | AGC | ATC | AGC | TAC | GAC | AGC | CGA | AAA | GTA | ACA | GAA | GAC 144 |
| Val | Ile | Phe | Asp | Ser | Ile | Ser | Tyr | Asp | Ser | Arg | Lys | Val | Thr | Glu | Asp |
| | | 25 | | | | | 40 | | | | 45 | | | | |
| ACT | CTT | TTT | TTT | GCA | AAA | GGC | GCT | GCC | TTT | AAA | AAA | GAA | TAC | CTT | CTT 192 |
| Thr | Leu | Phe | Phe | Ala | Lys | Gly | Ala | Ala | Phe | Lys | Lys | Glu | Tyr | Leu | Leu |
| | 50 | | | | 55 | | | | | 60 | | | | | |
| TCT | GCT | ATA | ACA | CAA | GGT | TTA | GCT | TGG | TAT | GTA | GCT | GAA | AAG | GAC | TAC 240 |
| Ser | Ala | Ile | Thr | Gln | Gly | Leu | Ala | Trp | Tyr | Val | Ala | Glu | Lys | Asp | Tyr |
| 65 | | | | | 70 | | | | 75 | | | | | | |
| GAA | GTC | GAT | ATC | CCT | GTC | ATC | ATT | GTG | AAC | GAT | ATA | AAG | AAA | GCC | ATG 288 |
| Glu | Val | Asp | Ile | Pro | Val | Ile | Ile | Val | Asn | Asp | Ile | Lys | Lys | Ala | Met |
| | | | | 85 | | | | | 90 | | | | | 95 | |
| AGT | TTG | ATT | GCC | ATG | GAG | TTC | TAT | GGT | AAT | CCA | CAA | GAG | AAA | CTC | AAA 336 |
| Ser | Leu | Ile | Ala | Met | Glu | Phe | Tyr | Gly | Asn | Pro | Gln | Glu | Lys | Leu | Lys |
| | | | 100 | | | | | 105 | | | | | 110 | | |
| CTC | CTT | GCC | TTT | ACT | GGT | ACT | AAG | GGT | AAG | ACA | ACA | GCA | ACC | TAT | TTC 384 |
| Leu | Leu | Ala | Phe | Thr | Gly | Thr | Lys | Gly | Lys | Thr | Thr | Ala | Thr | Tyr | Phe |
| | | 115 | | | | | 120 | | | | | 125 | | | |
| GCC | TAT | AAC | ATC | TTA | TCT | CAA | GGG | CAT | AGA | CCT | GCT | ATG | TTG | TCG | ACC 432 |
| Ala | Tyr | Asn | Ile | Leu | Ser | Gln | Gly | His | Arg | Pro | Ala | Met | Leu | Ser | Thr |
| | 130 | | | | | 135 | | | | | 140 | | | | |
| ATG | AAC | ACA | ACT | CTT | GAT | GGC | GAG | ACT | TTC | TTT | AAG | TCA | GCG | TTG | ACA 480 |
| Met | Asn | Thr | Thr | Leu | Asp | Gly | Glu | Thr | Phe | Phe | Lys | Ser | Ala | Leu | Thr |
| 145 | | | | | 150 | | | | | 155 | | | | | 160 |
| ACC | CCT | GAG | AGT | ATT | GAC | CTC | TTT | GAC | ATG | ATG | AAT | CAG | GCT | GTG | CAA 528 |
| Thr | Pro | Glu | Ser | Ile | Asp | Leu | Phe | Asp | Met | Met | Asn | Gln | Ala | Val | Gln |
| | | | | 165 | | | | | 170 | | | | | 175 | |
| AAT | GAC | CGT | ACC | CAC | CTC | ATC | ATG | GAA | GTC | TCC | AGT | CAA | GCC | TAT | CTA 576 |
| Asn | Asp | Arg | Thr | His | Leu | Ile | Met | Glu | Val | Ser | Ser | Gln | Ala | Tyr | Leu |
| | | | 180 | | | | | 185 | | | | | 190 | | |
| GTC | CAT | CGA | GTC | TAT | GGA | CTG | ACC | TTT | GAT | GTA | GGA | GTC | TTT | CTT | AAC 624 |
| Val | His | Arg | Val | Tyr | Gly | Leu | Thr | Phe | Asp | Val | Gly | Val | Phe | Leu | Asn |
| | | 195 | | | | | 200 | | | | | 205 | | | |
| ATC | ACT | CCT | GAC | CAT | ATC | GGC | CCG | ATT | GAA | CAC | CCT | AGC | TTT | GAA | GAC 672 |
| Ile | Thr | Pro | Asp | His | Ile | Gly | Pro | Ile | Glu | His | Pro | Ser | Phe | Glu | Asp |
| | 210 | | | | | 215 | | | | | 220 | | | | |
| TAT | TTC | TAC | CAC | AAG | CGT | CTC | TTG | ATG | GAA | AAT | AGC | CGA | GCA | GTC | ATC 720 |
| Tyr | Phe | Tyr | His | Lys | Arg | Leu | Leu | Met | Glu | Asn | Ser | Arg | Ala | Val | Ile |
| 225 | | | | 230 | | | | | 235 | | | | | | 240 |
| ATT | AAC | AGT | GAC | ATG | GAC | CAC | TTC | TCA | GTC | TTG | AAA | GAA | CAG | GTT | GAA 768 |
| Ile | Asn | Ser | Asp | Met | Asp | His | Phe | Ser | Val | Leu | Lys | Glu | Gln | Val | Glu |
| | | | | 245 | | | | | 250 | | | | | 255 | |
| GAT | CAA | GAC | CAT | GAT | TTC | TAT | GGT | AGC | CAA | TTT | GAT | AAC | CAA | ATC | GAG 816 |
| Asp | Gln | Asp | His | Asp | Phe | Tyr | Gly | Ser | Gln | Phe | Asp | Asn | Gln | Ile | Glu |
| | | | 260 | | | | | 265 | | | | | 270 | | |
| AAT | TCC | AAA | GCC | TTT | AGC | TTT | TCA | GCT | ACG | GGT | AAA | CTC | GCT | GGA | GAT 864 |
| Asn | Ser | Lys | Ala | Phe | Ser | Phe | Ser | Ala | Thr | Gly | Lys | Leu | Ala | Gly | Asp |
| | | 275 | | | | | 280 | | | | | 285 | | | |
| TAT | GAT | ATC | CAA | CTC | ATT | GGC | AAC | TTC | AAC | CAA | GAA | AAT | GCA | GTT | GCT 912 |
| Tyr | Asp | Ile | Gln | Leu | Ile | Gly | Asn | Phe | Asn | Gln | Glu | Asn | Ala | Val | Ala |
| | 290 | | | | | 295 | | | | | 300 | | | | |
| GCT | GGA | CTT | GCT | TGT | CTC | CGT | CTC | GGA | GCA | AGT | CTT | GAG | GAC | ATC | AAA 960 |
| Ala | Gly | Leu | Ala | Cys | Leu | Arg | Leu | Gly | Ala | Ser | Leu | Glu | Asp | Ile | Lys |
| 305 | | | | 310 | | | | | 315 | | | | | 320 | |
| AAA | GGC | ATC | GCT | GCA | ACC | CGC | GTT | CCT | GGT | CGT | ATG | GAA | GTC | CTC | ACT 1008 |
| Lys | Gly | Ile | Ala | Ala | Thr | Arg | Val | Pro | Gly | Arg | Met | Glu | Val | Leu | Thr |
| | | | | 325 | | | | | 330 | | | | | 335 | |
| CAG | AAA | AAT | GGA | GCC | AAG | GTC | TTC | ATC | GAC | TAT | GCC | CAC | AAT | GGG | GAT 1056 |
| Gln | Lys | Asn | Gly | Ala | Lys | Val | Phe | Ile | Asp | Tyr | Ala | His | Asn | Gly | Asp |
| | | | 340 | | | | | 345 | | | | | 350 | | |

| | | | | | | | | | | | | | | | |
|---|---|---|---|---|---|---|---|---|---|---|---|---|---|---|---|
| AGT | CTG | AAA | AAA | CTC | ATC | AAT | GTG | GTT | GAA | ACT | CAT | CAA | ACC | GGA | AAG | 1104
| Ser | Leu | Lys | Lys | Leu | Ile | Asn | Val | Val | Glu | Thr | His | Gln | Thr | Gly | Lys |
| | | 355 | | | | | 360 | | | | | 365 | | | |
| ATT | GCT | CTG | GTT | CTG | GGA | TCA | ACA | GGA | AAC | AAG | GGA | GAA | AGT | CGT | CGT | 1152
| Ile | Ala | Leu | Val | Leu | Gly | Ser | Thr | Gly | Asn | Lys | Gly | Glu | Ser | Arg | Arg |
| | | 370 | | | | 375 | | | | | 380 | | | | |
| AAG | GAC | TTT | GGC | CTC | CTC | CTC | AAT | CAA | CAC | CCT | GAG | ATT | CAA | GTC | TTT | 1200
| Lys | Asp | Phe | Gly | Leu | Leu | Leu | Asn | Gln | His | Pro | Glu | Ile | Gln | Val | Phe |
| 385 | | | | | 390 | | | | | 395 | | | | | 400 |
| CTG | ACT | GCT | GAT | GAC | CCT | AAC | TAT | GAA | GAC | CCA | ATG | GCC | ATT | GCA | GAT | 1248
| Leu | Thr | Ala | Asp | Asp | Pro | Asn | Tyr | Glu | Asp | Pro | Met | Ala | Ile | Ala | Asp |
| | | | | 405 | | | | | 410 | | | | | 415 | |
| GAA | ATT | AGT | AGC | TAC | ATC | AAT | CAT | CCT | GTT | GAA | AAG | ATT | GCG | GAT | CGC | 1296
| Glu | Ile | Ser | Ser | Tyr | Ile | Asn | His | Pro | Val | Glu | Lys | Ile | Ala | Asp | Arg |
| | | | 420 | | | | | 425 | | | | | 430 | | |
| CAA | GAA | GCC | ATC | AAG | GCG | GCA | ATG | GCT | ATC | ACA | AAT | CAC | GAA | TTA | GAT | 1344
| Gln | Glu | Ala | Ile | Lys | Ala | Ala | Met | Ala | Ile | Thr | Asn | His | Glu | Leu | Asp |
| | | 435 | | | | | 440 | | | | | 445 | | | |
| GCA | GTT | ATT | ATT | GCG | GGT | AAG | GGA | GCC | GAT | TGT | TAC | CAA | ATC | ATC | CAG | 1392
| Ala | Val | Ile | Ile | Ala | Gly | Lys | Gly | Ala | Asp | Cys | Tyr | Gln | Ile | Ile | Gln |
| | | 450 | | | | 455 | | | | | 460 | | | | |
| GGC | AAG | AAA | GAA | TCC | TAC | CCA | GGA | GAT | ACA | GCC | GTC | GCA | GAA | AAT | TAT | 1440
| Gly | Lys | Lys | Glu | Ser | Tyr | Pro | Gly | Asp | Thr | Ala | Val | Ala | Glu | Asn | Tyr |
| 465 | | | | | 470 | | | | | 475 | | | | | 480 |
| TTA | | | | | | | | | | | | | | | | 1446
| Leu | | | | | | | | | | | | | | | |

In another embodiment the present invention is a protein molecule comprising the sequence identified as SEQ ID NO. 2:

| | | | | | | | | | | | | | | |
|---|---|---|---|---|---|---|---|---|---|---|---|---|---|---|
| Met | Ile | Lys | Ile | Glu | Thr | Val | Leu | Asp | Ile | Leu | Lys | Lys | Asp | Gly | Leu |
| 1 | | | | 5 | | | | | 10 | | | | | 15 | |
| Phe | Arg | Glu | Ile | Ile | Asp | Gln | Gly | His | Tyr | His | Tyr | Asn | Tyr | Ser | Lys |
| | | | 20 | | | | | 25 | | | | | 30 | | |
| Val | Ile | Phe | Asp | Ser | Ile | Ser | Tyr | Asp | Ser | Arg | Lys | Val | Thr | Glu | Asp |
| | | 35 | | | | | 40 | | | | | 45 | | | |
| Thr | Leu | Phe | Phe | Ala | Lys | Gly | Ala | Ala | Phe | Lys | Lys | Glu | Tyr | Leu | Leu |
| | 50 | | | | | 55 | | | | | 60 | | | | |
| Ser | Ala | Ile | Thr | Gln | Gly | Leu | Ala | Trp | Tyr | Val | Ala | Glu | Lys | Asp | Tyr |
| 65 | | | | | 70 | | | | | 75 | | | | | 80 |
| Glu | Val | Asp | Ile | Pro | Val | Ile | Ile | Val | Asn | Asp | Ile | Lys | Lys | Ala | Met |
| | | | | 85 | | | | | 90 | | | | | 95 | |
| Ser | Leu | Ile | Ala | Met | Glu | Phe | Tyr | Gly | Asn | Pro | Gln | Glu | Lys | Leu | Lys |
| | | | 100 | | | | | 105 | | | | | 110 | | |
| Leu | Leu | Ala | Phe | Thr | Gly | Thr | Lys | Gly | Lys | Thr | Thr | Ala | Thr | Tyr | Phe |
| | | 115 | | | | | 120 | | | | | 125 | | | |
| Ala | Tyr | Asn | Ile | Leu | Ser | Gln | Gly | His | Arg | Pro | Ala | Met | Leu | Ser | Thr |
| | 130 | | | | | 135 | | | | | 140 | | | | |
| Met | Asn | Thr | Thr | Leu | Asp | Gly | Glu | Thr | Phe | Phe | Lys | Ser | Ala | Leu | Thr |
| 145 | | | | | 150 | | | | | 155 | | | | | 160 |
| Thr | Pro | Glu | Ser | Ile | Asp | Leu | Phe | Asp | Met | Met | Asn | Gln | Ala | Val | Gln |
| | | | | 165 | | | | | 170 | | | | | 175 | |
| Asn | Asp | Arg | Thr | His | Leu | Ile | Met | Glu | Val | Ser | Ser | Gln | Ala | Tyr | Leu |
| | | | 180 | | | | | 185 | | | | | 190 | | |
| Val | His | Arg | Val | Tyr | Gly | Leu | Thr | Phe | Asp | Val | Gly | Val | Phe | Leu | Asn |
| | | 195 | | | | | 200 | | | | | 205 | | | |
| Ile | Thr | Pro | Asp | His | Ile | Gly | Pro | Ile | Glu | His | Pro | Ser | Phe | Glu | Asp |
| | 210 | | | | | 215 | | | | | 220 | | | | |

Tyr Phe Tyr His Lys Arg Leu Leu Met Glu Asn Ser Arg Ala Val Ile
225                 230                  235                      240

Ile Asn Ser Asp Met Asp His Phe Ser Val Leu Lys Glu Gln Val Glu
            245                  250                  255

Asp Gln Asp His Asp Phe Tyr Gly Ser Gln Phe Asp Asn Gln Ile Glu
            260                  265                  270

Asn Ser Lys Ala Phe Ser Phe Ser Ala Thr Gly Lys Leu Ala Gly Asp
        275                  280                  285

Tyr Asp Ile Gln Leu Ile Gly Asn Phe Asn Gln Glu Asn Ala Val Ala
    290                  295                  300

Ala Gly Leu Ala Cys Leu Arg Leu Gly Ala Ser Leu Glu Asp Ile Lys
305                  310                  315                  320

Lys Gly Ile Ala Ala Thr Arg Val Pro Gly Arg Met Glu Val Leu Thr
                325                  330                  335

Gln Lys Asn Gly Ala Lys Val Phe Ile Asp Tyr Ala His Asn Gly Asp
            340                  345                  350

Ser Leu Lys Lys Leu Ile Asn Val Val Glu Thr His Gln Thr Gly Lys
        355                  360                  365

Ile Ala Leu Val Leu Gly Ser Thr Gly Asn Lys Gly Glu Ser Arg Arg
    370                  375                  380

Lys Asp Phe Gly Leu Leu Leu Asn Gln His Pro Glu Ile Gln Val Phe
385                  390                  395                  400

Leu Thr Ala Asp Asp Pro Asn Tyr Glu Asp Pro Met Ala Ile Ala Asp
            405                  410                  415

Glu Ile Ser Ser Tyr Ile Asn His Pro Val Glu Lys Ile Ala Asp Arg
            420                  425                  430

Gln Glu Ala Ile Lys Ala Ala Met Ala Ile Thr Asn His Glu Leu Asp
        435                  440                  445

Ala Val Ile Ile Ala Gly Lys Gly Ala Asp Cys Tyr Gln Ile Ile Gln
    450                  455                  460

Gly Lys Lys Glu Ser Tyr Pro Gly Asp Thr Ala Val Ala Glu Asn Tyr
465                  470                  475                  480

Leu

In a further embodiment the present invention relates to a ribonucleic acid molecule comprising the sequence identified as SEQ ID NO. 3:

AUGAUUAAGA UUGAAACCGU AUUAGAUAUU UUAAAGAAAG AUGGCCUUUU UCGCGAAAUU 60

AUUGACCAAG GUCAUUACCA CUACAACUAC AGCAAAGUUA UUUUUGAUAG CAUCAGCUAC 120

GACAGCCGAA AAGUAACAGA AGACACUCUU UUUUUUGCAA AAGGCGCUGC CUUUAAAAAA 180

GAAUACCUUC UUUCUGCUAU AACACAAGGU UUAGCUUGGU AUGUAGCUGA AAAGGACUAC 240

GAAGUCGAUA UCCCUGUCAU CAUUGUGAAC GAUAUAAAGA AAGCCAUGAG UUUGAUUGCC 300

AUGGAGUUCU AUGGUAAUCC ACAAGAGAAA CUCAAACUCC UUGCCUUUAC UGGUACUAAG 360

GGUAAGACAA CAGCAACCUA UUUCGCCUAU AACAUCUUAU CUCAAGGGCA UAGACCUGCU 420

AUGUUGUCGA CCAUGAACAC AACUCUUGAU GGCGAGACUU UCUUUAAGUC AGCGUUGACA 480

ACCCCUGAGA GUAUUGACCU CUUUGACAUG AUGAAUCAGG CUGUGCAAAA UGACCGUACC 540

-continued

```
CACCUCAUCA UGGAAGUCUC CAGUCAAGCC UAUCUAGUCC AUCGAGUCUA UGGACUGACC 600

UUUGAUGUAG GAGUCUUUCU UAACAUCACU CCUGACCAUA UCGGCCCGAU UGAACACCCU 660

AGCUUUGAAG ACUAUUUCUA CCACAAGCGU CUCUUGAUGG AAAAUAGCCG AGCAGUCAUC 620

AUUAACAGUG ACAUGGACCA CUUCUCAGUC UUGAAAGAAC AGGUUGAAGA UCAAGACCAU 780

GAUUUCUAUG GUAGCCAAUU UGAUAACCAA AUCGAGAAUU CCAAAGCCUU UAGCUUUUCA 840

GCUACGGGUA AACUCGCUGG AGAUUAUGAU AUCCAACUCA UUGGCAACUU CAACCAAGAA 900

AAUGCAGUUG CUGCUGGACU UGCUUGUCUC CGUCUCGGAG CAAGUCUUGA GGACAUCAAA 960

AAAGGCAUCG CUGCAACCCG CGUUCCUGGU CGUAUGGAAG UCCUCACUCA GAAAAAUGGA 1020

GCCAAGGUCU UCAUCGACUA UGCCCACAAU GGGGAUAGUC UGAAAAAACU CAUGAAUGUG 1080

GUUGAAACUC AUCAAACCGG AAAGAUUGCU CUGGUUCUGG GAUCAACAGG AAACAAGGGA 1140

GAAAGUCGUC GUAAGGACUU UGGCCUCCUC CUCAAUCAAC ACCCUGAGAU UCAAGUCUUU 1200

CUGACUGCUG AUGACCCUAA CUAUGAAGAC CCAAUGGCCA UUGCAGAUGA AAUUAGUAGC 1260

UACAUCAAUC AUCCUGUUGA AAAGAUUGCG GAUCGCCAAG AAGCCAUCAA GGCGGCAAUG 1320

GCUAUCACAA AUCACGAAUU AGAUGCAGUU AUUAUUGCGG GUAAGGGAGC CGAUUGUUAC 1380

CAAAUCAUCC AGGGCAAGAA AGAAUCCUAC CCAGGAGAUA CAGCCGUCGC AGAAAAUUAU 1440

UUUAUAA
```

In yet another embodiment, the present invention is a recombinant DNA vector which incorporates the *Streptococcus pneumoniae* murE gene in operable linkage to gene expression sequences which enable the murE gene to be transcribed and translated in a host cell.

In still another embodiment the present invention relates to homologous or heterologous host cells which have been transformed or transfected with the cloned murE gene of *Streptococcus pneumoniae* such that the murE gene is expressed in the host cell.

In a still further embodiment, the present invention relates to a method for identifying inhibitory compounds which target the MurE protein of *Streptococcus pneumoniae*.

DESCRIPTION OF THE DRAWING

Figure. Plasmid pPSR10, which is useful for high level expression of the *Streptococcus pneumoniae* murE gene in heterologous or homologous procaryotic host cells.

DEFINITIONS

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "stringency" refers to a set of hybridization conditions which may be varied in order to vary the degree of nucleic acid hybridization with another nucleic acid.

DETAILED DESCRIPTION

The murE gene of *Streptococcus pneumoniae* encodes an enzyme involved in stem peptide biosynthesis. The stem peptide pathway is necessary for the synthesis of the peptidoglycan layer which is part of the bacterial cell wall. There are at least 10 steps involved in stem peptide biosynthesis. The murE gene encodes uridine-diphosphate-N-acetyulmuramoyl-L-alanyl-D-glutamate:L-lysine ligase (SEQ ID NO. 2), which catalyzes the addition of L-lysine to UDPMurNAc-L-Ala-D-Glu forming UDPMurNAc-L-Ala-D-Glu-L-lys.

The murE gene of *Streptococcus pneumoniae* comprises a DNA sequence of 1443 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

Gene Isolation Procedures

Those skilled in the art will recogize that the gene may be obtained by a plurality of applicable genetic and recombinant DNA techniques including, for example, polymerase chain reaction (PCR) amplification, or de novo DNA synthesis.(See e.g., Sambrook et al. supra, Chap. 14)

Methods for constructing gene libraries in a suitable vector such as a plasmid or phage for propagation in procaryotic or eucaryotic cells are well known to those skilled in the art. [See e.g. J. Sambrook et al. *Molecular Cloning*, 2d Ed. (1989)]. Suitable cloning vectors are widely available.

Skilled artisans will recognize that the murE gene of *Streptococcus pneumoniae* or fragment thereof could also be isolated by PCR amplification starting with *Streptococcus pneumoniae* genomic DNA and oligonucleotide primers targeted to any suitable region of SEQ ID NO. 1. Methods for PCR amplification are widely known in the art. See e.g. *PCR Protocols: A Guide to Method and Application*, Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn.). A positive result is determined by the presence of an appropriately-sized DNA fragment following agarose gel electrophoresis.

Protein Production Methods

One of the embodiments of the present invention is the purified protein encoded by the murE gene or functionally related proteins of *Streptococcus pneumoniae*.

Skilled artisans will recognize that the proteins of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, N.Y., 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably −20° C. for thirty minutes followed by thirty minutes at 0° C.

The protein of the present invention can also be produced by recombinant DNA methods using the cloned murE gene of *Streptococcus pneumoniae*. Recombinant methods are preferred if a high yield is desired. Expression of the cloned murE gene can be carried out in a variety of suitable host cells well known to those skilled in the art. The murE gene is introduced into a host cell by any suitable means, well known to those skilled in the art. While chromosomal integration of the cloned murE gene is within the scope of the present invention, it is preferred that the gene be cloned into a suitable extra-chromosomally maintained expression vector so that the coding region of the murE gene is operably linked to a constitutive or inducible promoter.

The basic steps in the recombinant production of the MurE protein are:

a) constructing a natural, synthetic or semi-synthetic DNA encoding MurE protein;

b) integrating said DNA into an expression vector in a manner suitable for expressing the MurE protein, either alone or as a fusion protein;

c) transforming an appropriate eukaryotic or prokaryotic host cell with said expression vector, d) culturing said transformed host cell in a manner to express the MurE protein; and e) recovering and purifying the MurE protein by any suitable means.

Expressing Recombinant MurE Protein in Procaryotic and Eucaryotic Host Cells

In general, prokaryotes are used for cloning DNA sequences and for constructing the vectors of the present invention. Prokaryotes are also employed in the production of the MurE protein. For example, the *Escherichia coli* K12 strain 294 (ATCC No. 31446) is particularly useful for the prokaryotic expression of foreign proteins. Other strains of *E. coli*, bacilli such as *Bacillus subtilis*, enterobacteriaceae such as *Salmonella typhimurium* or *Serratia marcescans*, various Pseudomonas species and other bacteria, such as Streptomyces, may also be employed in the cloning and expression of the proteins of this invention.

Promoters suitable for driving the expression of gene sequences in prokaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector PATHI (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes,* American Chemical Society, Washington, D.C. (1990).

In addition to prokaryotes, mammalian host cells and eukaryotic microbes such as yeast may also be used. The simple eucaryote *Saccharomyces cerevisiae,* is the most commonly used eukaryotic microorganism, although a number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced MurE Protein

An expression vector carrying the cloned murE gene of *Streptococcus pneuinoniae* is transformed or transfected into a suitable host cell using standard methods. Cells which contain the vector are then propagated under conditions suitable for expression of the MurE protein. The recombinantly produced protein may be purified from cellular extracts of transformed cells by any suitable means. In a preferred process for protein purification the murE gene is modified at the 5' end to incorporate several histidine residues at the amino terminus of the MurE protein product. The histidine tag enables a single-step protein purification method referred to as "immobilized metal ion affinity chromatography" (IMAC), essentially as described in U.S. Pat. No. 4,569,794 which hereby is incorporated by reference.

Other embodiments of the present invention comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The murE gene, which comprises nucleic acid encoding SEQ ID NO:2, may be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the murE gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis. A Practical Approach,* (1984).]

In an alternative methodology, murE DNA sequences comprising a portion or all of SEQ ID NO:1 can be generated from *Streptococcus pneumoniae* genomic DNA using suitable oligonucleotide primers complementary to SEQ ID NO:1 or region therein, utilizing the polymerase chain reaction as described in U.S. Pat. No. 4,889,818, which is incorporated herein by reference. Protocols for performing the PCR are disclosed in, *PCR Protocols: A Guide to Method and Applications,* Ed. Michael A. Innis et al., Academic Press, Inc. (1990), which hereby is incorporated by reference.

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to *Streptococcus pneumoniae* DNA or mRNA encoding murE, is provided. Preferably, the 18 or more base pair compound is DNA.

These probes and primers can be prepared enzymatically as will be well known to those skilled in the art (See e.g. Sambrook et al. supra). In a most preferred embodiment these probes and primers are synthesized using chemical means as described above.

Another aspect of the present invention is recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence SEQ ID NO:1. Plasmid pPSR10 is an especially preferred DNA vector of the present invention.

The skilled artisan understands that choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers, metabolic markers, or the like), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they may be the basis for high level, regulatable expression of an operably linked gene. The skilled artisan will recognize a number of inducible promoters and inducers, for example, carbon source, metal ions, heat, and others. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is any strain of *E. coli* which can accomodate high level expression of a gene(s) introduced by transformation or transfection. Preferred vectors for expression are those which comprise SEQ ID NO:1. An especially preferred expression vector for use in *E. coli* is plasmid pPSR10, which comprises SEQ ID NO:1. (See Figure). Transformed host cells may be cultured under conditions well known to skilled artisans such that SEQ ID NO:2 is expressed, thereby producing MurE protein in the recombinant host cell.

For the purpose of identifying or developing inhibitors of the stem peptide pathway, it would be desirable to determine those agents which inhibit the murE step. A method for determining whether a substance will inhibit the enzymatic reaction catalyzed by the MurE protein comprises contacting the MurE protein with a test substance and monitoring MurE enzyme activity by any suitable means.

The instant invention provides such a screening system useful for discovering agents which inhibit the MurE protein product, said screening system comprising the steps of:
a) preparing MurE enzyme;
b) exposing said MurE enzyme to a test inhibitor;
c) introducing substrate; and
d) quantifying the loss of activity of said MurE enzyme.

Utilization of the screening system described above provides a means to determine compounds which interfere with stem peptide biosynthesis. This screening system may be adapted to automated procedures such as a PANDEX® (Baxter-Dade Diagnostics) system allowing for efficient high-volume screening of potential therapeutic agents.

In such a screening protocol MurE enzyme is prepared as described herein, preferably using recombinant DNA technology. A sample of a test compound is then introduced into the reaction vessel containing the MurE enzyme, followed by the addition of enzyme substrate. In the alternative, the substrate may be added simultaneously with the test compound. For example, in a preferred method of the invention, radioactively or chemically-labeled substrate may be used. The products of the enzymatic reaction are then quantitated for the chemical label or radioactivity. The absence or diminution of the chemical label or radioactivity indicates the degree to which the reaction is inhibited.

Skilled artisans will recognize that $IC_{50}$ values are dependent on the selectivity of the compound tested. For example, a compound with an $IC_{50}$ which is less than 10 nM is generally considered an excellent candidate for drug therapy. However, a compound which has a lower affinity, but is selective for a particular target, may be an even better candidate. The skilled artisan will recognize that any information regarding inhibitory activity or selectivity of a particular compound is beneficial in the pharmaceutical development of drugs.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra.

The following examples more fully describe the present invention. Those skilled in the art will recognize that the particular reagents, equipment, and procedures described are merely illustrative and are not intended to limit the present invention in any manner.

EXAMPLE 1

Construction of DNA Vector for Expressing *Streptococcus pneumoniae* murE Gene in Homologous or Heterologous Host Plasmid pPSR10 (See FIG. 1) is an approximately 7500 base pair expression vector suitable for expressing the murE gene of *S. pneumoniae* in the procaryotic host *E. coli*. This plasmid contains an origin of replication (Ori), an ampicillin resistance gene (Amp) useful for selecting cells which have incorporated the vector following a tranformation procedure, and further comprises the lacI gene for repression of the lac operon, as well as the T7 promoter and T7 terminator sequences in operable linkage to the coding region of the murE gene. Parent plasmid pET11A (obtained from Novogen, Madison, Wis.) was linearized by restriction with endonucleases NdeI and BamHI. Linearized pET11A was ligated to a DNA fragment bearing NdeI and BamHI sticky ends and comprising the coding region of the *S. pneumoniae* murE gene.

The murE gene ligated into pPSR10 was modified at the 5' end (amino terminus of encoded protein) in order to simplify purification of the encoded MurE protein product.

For this purpose, an oligonucleotide encoding 8 histidine residues and a factor Xa cleavage site was inserted after the ATG start codon at nucleotide positions 1 to 3 of SEQ ID NO: 1. Placement of the histidine residues at the amino terminus of the encoded protein does not affect its activity and serves only to enable the IMAC one-step protein purification procedure (See below).

EXAMPLE 2
Expression of *Streptococcus pneumoniae* murE Gene in *Echerichia coli* and Purification of MurE Enzyme Plasmid pPSR10 was transformed into *E. coli* BL21 (DE3) (hsdS gal λcIts857 ind1Sam7nin5lacUV5-T7gene 1) using standard methods. Transformants, selected for resistance to ampicillin, were chosen at random and tested for the presence of pPSR10 by agarose gel electrophoresis using quick plasmid preparations. Colonies which contained PPSR10 were grown in TY broth and the protein product encoded by the murE gene was purified by immobilized metal ion affinity chromatography (IMAC), essentially as described in U.S. Pat. No. 4,569,794, the entire contents of which is hereby incorporated by reference.

Briefly, the IMAC column was prepared as follows. A metal-free chelating resin (e.g. SEPHAROSE 6B IDA, Pharmacia) was washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin were saturated with colored metal ion. The column was then ready to receive a crude cellular extract containing the MurE protein product encoded by pPSR10.

After removing unbound proteins and other materials by washing the column with suitable buffer, pH 7.5, the bound protein was eluted in buffer at pH 4.3 essentially as described in U.S. Pat. No. 4,569,794.

EXAMPLE 3
Biochemical Assay for Inhibitors of *Streptococcus pneumoniae* MurE Enzyme Product The activity of the enzyme encoded by murE was assayed by monitoring the appearance of the enzyme product, UDP-MurNAc-L-Ala-D-Glu-L-Lys, using high-pressure liquid chromatography detection (HPLC). The enzyme reaction consisted of 0.1M Tris/HCl pH 8.6, 0.1M $MgCl_2$, 5 mM ATP, 50 µM UDP-MurNAc-L-Ala-D-Glu, 0.1 mM Lysine and enzyme in a final volume of 50 µl. Substrate UDP-MurNAc-L-Ala-D-Glu was purified as described in B. Flouret et al., *Reverse-phase high-pressure liquid chromatography of uridine diphosphate N-Acetylmuramyl peptide precursors of bacterial cell wall peptidoglycan*. Anal. Biochem. 114, 59–63 (1981). The mixture was incubated for 30 min. at 37° C., and the reaction terminated with the addition of 10 µl of glacial acetic acid. The amount of product generated was determined by HPLC, essentially as described in Flouret et.al. (Id.). Briefly, the nucleotide precursors were extracted in the cold by trichloroacetic acid and purified by gel filtration on fine SEPHADEX G-25. Under these conditions the UDP-MurNac derivatives are eluted with water in a volume slightly larger than the exclusion volume of the column. Separation and further purification of UDP-MurNAc derivatives were carried out by ion-exchange chromatography on Dowex AG1×2 (200–400 mesh) according to the method of Park & Chatterjee, *Methods in Enzymology*, 8, 466–472 (Academic Press, N.Y. 1966). HPLC analyses were performed with a Waters Associates apparatus consisting of two Model 6000 A solvent delivering systems, a Model 660 solvent programmer, and a Model 450 variable wavelength detector which monitored the eluant at 220 nm or at 262 nm. Peaks were recorded and integrated with a Spectra Physics SP 4100 model computing integrator (Spectra Physics, Santa Clara, Calif.).

Inhibition studies are carried out using the same reaction conditions described in the preceding paragraph. Compounds to be studied for inhibitory activity are added to final concentrations of between 1 mM and 10 mM.

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1446 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1443

( x i ) SEQUENCE DESCRIPTION: SEQ ID NO:1:

```
ATG  ATT  AAG  ATT  GAA  ACC  GTA  TTA  GAT  ATT  TTA  AAG  AAA  GAT  GGC  CTT        4 8
Met  Ile  Lys  Ile  Glu  Thr  Val  Leu  Asp  Ile  Leu  Lys  Lys  Asp  Gly  Leu
 1             5                        10                       15

TTT  CGC  GAA  ATT  ATT  GAC  CAA  GGT  CAT  TAC  CAC  TAC  AAC  TAC  AGC  AAA        9 6
Phe  Arg  Glu  Ile  Ile  Asp  Gln  Gly  His  Tyr  His  Tyr  Asn  Tyr  Ser  Lys
              20                       25                       30

GTT  ATT  TTT  GAT  AGC  ATC  AGC  TAC  GAC  AGC  CGA  AAA  GTA  ACA  GAA  GAC       144
```

|   |   |   |   |   |   |   |   |   |   |   |   |   |   |   |   |     |
|---|---|---|---|---|---|---|---|---|---|---|---|---|---|---|---|-----|
| Val | Ile | Phe | Asp | Ser | Ile | Ser | Tyr | Asp | Ser | Arg | Lys | Val | Thr | Glu | Asp |  |
|     |     | 35  |     |     |     | 40  |     |     |     |     | 45  |     |     |     |     |  |

```
ACT  CTT  TTT  TTT  GCA  AAA  GGC  GCT  GCC  TTT  AAA  AAA  GAA  TAC  CTT  CTT    192
Thr  Leu  Phe  Phe  Ala  Lys  Gly  Ala  Ala  Phe  Lys  Lys  Glu  Tyr  Leu  Leu
     50                  55                       60

TCT  GCT  ATA  ACA  CAA  GGT  TTA  GCT  TGG  TAT  GTA  GCT  GAA  AAG  GAC  TAC    240
Ser  Ala  Ile  Thr  Gln  Gly  Leu  Ala  Trp  Tyr  Val  Ala  Glu  Lys  Asp  Tyr
65             70                       75                            80

GAA  GTC  GAT  ATC  CCT  GTC  ATC  ATT  GTG  AAC  GAT  ATA  AAG  AAA  GCC  ATG    288
Glu  Val  Asp  Ile  Pro  Val  Ile  Ile  Val  Asn  Asp  Ile  Lys  Lys  Ala  Met
                    85                       90                       95

AGT  TTG  ATT  GCC  ATG  GAG  TTC  TAT  GGT  AAT  CCA  CAA  GAG  AAA  CTC  AAA    336
Ser  Leu  Ile  Ala  Met  Glu  Phe  Tyr  Gly  Asn  Pro  Gln  Glu  Lys  Leu  Lys
               100                      105                      110

CTC  CTT  GCC  TTT  ACT  GGT  ACT  AAG  GGT  AAG  ACA  ACA  GCA  ACC  TAT  TTC    384
Leu  Leu  Ala  Phe  Thr  Gly  Thr  Lys  Gly  Lys  Thr  Thr  Ala  Thr  Tyr  Phe
          115                      120                      125

GCC  TAT  AAC  ATC  TTA  TCT  CAA  GGG  CAT  AGA  CCT  GCT  ATG  TTG  TCG  ACC    432
Ala  Tyr  Asn  Ile  Leu  Ser  Gln  Gly  His  Arg  Pro  Ala  Met  Leu  Ser  Thr
     130                      135                      140

ATG  AAC  ACA  ACT  CTT  GAT  GGC  GAG  ACT  TTC  TTT  AAG  TCA  GCG  TTG  ACA    480
Met  Asn  Thr  Thr  Leu  Asp  Gly  Glu  Thr  Phe  Phe  Lys  Ser  Ala  Leu  Thr
145                      150                      155                      160

ACC  CCT  GAG  AGT  ATT  GAC  CTC  TTT  GAC  ATG  ATG  AAT  CAG  GCT  GTG  CAA    528
Thr  Pro  Glu  Ser  Ile  Asp  Leu  Phe  Asp  Met  Met  Asn  Gln  Ala  Val  Gln
               165                      170                      175

AAT  GAC  CGT  ACC  CAC  CTC  ATC  ATG  GAA  GTC  TCC  AGT  CAA  GCC  TAT  CTA    576
Asn  Asp  Arg  Thr  His  Leu  Ile  Met  Glu  Val  Ser  Ser  Gln  Ala  Tyr  Leu
          180                      185                      190

GTC  CAT  CGA  GTC  TAT  GGA  CTG  ACC  TTT  GAT  GTA  GGA  GTC  TTT  CTT  AAC    624
Val  His  Arg  Val  Tyr  Gly  Leu  Thr  Phe  Asp  Val  Gly  Val  Phe  Leu  Asn
     195                      200                      205

ATC  ACT  CCT  GAC  CAT  ATC  GGC  CCG  ATT  GAA  CAC  CCT  AGC  TTT  GAA  GAC    672
Ile  Thr  Pro  Asp  His  Ile  Gly  Pro  Ile  Glu  His  Pro  Ser  Phe  Glu  Asp
     210                      215                      220

TAT  TTC  TAC  CAC  AAG  CGT  CTC  TTG  ATG  GAA  AAT  AGC  CGA  GCA  GTC  ATC    720
Tyr  Phe  Tyr  His  Lys  Arg  Leu  Leu  Met  Glu  Asn  Ser  Arg  Ala  Val  Ile
225                      230                      235                      240

ATT  AAC  AGT  GAC  ATG  GAC  CAC  TTC  TCA  GTC  TTG  AAA  GAA  CAG  GTT  GAA    768
Ile  Asn  Ser  Asp  Met  Asp  His  Phe  Ser  Val  Leu  Lys  Glu  Gln  Val  Glu
               245                      250                      255

GAT  CAA  GAC  CAT  GAT  TTC  TAT  GGT  AGC  CAA  TTT  GAT  AAC  CAA  ATC  GAG    816
Asp  Gln  Asp  His  Asp  Phe  Tyr  Gly  Ser  Gln  Phe  Asp  Asn  Gln  Ile  Glu
          260                      265                      270

AAT  TCC  AAA  GCC  TTT  AGC  TTT  TCA  GCT  ACG  GGT  AAA  CTC  GCT  GGA  GAT    864
Asn  Ser  Lys  Ala  Phe  Ser  Phe  Ser  Ala  Thr  Gly  Lys  Leu  Ala  Gly  Asp
     275                      280                      285

TAT  GAT  ATC  CAA  CTC  ATT  GGC  AAC  TTC  AAC  CAA  GAA  AAT  GCA  GTT  GCT    912
Tyr  Asp  Ile  Gln  Leu  Ile  Gly  Asn  Phe  Asn  Gln  Glu  Asn  Ala  Val  Ala
290                      295                      300

GCT  GGA  CTT  GCT  TGT  CTC  CGT  CTC  GGA  GCA  AGT  CTT  GAG  GAC  ATC  AAA    960
Ala  Gly  Leu  Ala  Cys  Leu  Arg  Leu  Gly  Ala  Ser  Leu  Glu  Asp  Ile  Lys
305                      310                      315                      320

AAA  GGC  ATC  GCT  GCA  ACC  CGC  GTT  CCT  GGT  CGT  ATG  GAA  GTC  CTC  ACT   1008
Lys  Gly  Ile  Ala  Ala  Thr  Arg  Val  Pro  Gly  Arg  Met  Glu  Val  Leu  Thr
               325                      330                      335

CAG  AAA  AAT  GGA  GCC  AAG  GTC  TTC  ATC  GAC  TAT  GCC  CAC  AAT  GGG  GAT   1056
Gln  Lys  Asn  Gly  Ala  Lys  Val  Phe  Ile  Asp  Tyr  Ala  His  Asn  Gly  Asp
          340                      345                      350

AGT  CTG  AAA  AAA  CTC  ATC  AAT  GTG  GTT  GAA  ACT  CAT  CAA  ACC  GGA  AAG   1104
```

| | | | | | | | | | | | | | | | | |
|---|---|---|---|---|---|---|---|---|---|---|---|---|---|---|---|---|
| Ser | Leu | Lys | Lys | Leu | Ile | Asn | Val | Val | Glu | Thr | His | Gln | Thr | Gly | Lys | |
| | | 355 | | | | 360 | | | | | | 365 | | | | |

| ATT | GCT | CTG | GTT | CTG | GGA | TCA | ACA | GGA | AAC | AAG | GGA | GAA | AGT | CGT | CGT | 1152 |
|---|---|---|---|---|---|---|---|---|---|---|---|---|---|---|---|---|
| Ile | Ala | Leu | Val | Leu | Gly | Ser | Thr | Gly | Asn | Lys | Gly | Glu | Ser | Arg | Arg | |
| | 370 | | | | 375 | | | | | 380 | | | | | | |

| AAG | GAC | TTT | GGC | CTC | CTC | CTC | AAT | CAA | CAC | CCT | GAG | ATT | CAA | GTC | TTT | 1200 |
|---|---|---|---|---|---|---|---|---|---|---|---|---|---|---|---|---|
| Lys | Asp | Phe | Gly | Leu | Leu | Leu | Asn | Gln | His | Pro | Glu | Ile | Gln | Val | Phe | |
| 385 | | | | | 390 | | | | | 395 | | | | | 400 | |

| CTG | ACT | GCT | GAT | GAC | CCT | AAC | TAT | GAA | GAC | CCA | ATG | GCC | ATT | GCA | GAT | 1248 |
|---|---|---|---|---|---|---|---|---|---|---|---|---|---|---|---|---|
| Leu | Thr | Ala | Asp | Asp | Pro | Asn | Tyr | Glu | Asp | Pro | Met | Ala | Ile | Ala | Asp | |
| | | | | 405 | | | | | 410 | | | | | 415 | | |

| GAA | ATT | AGT | AGC | TAC | ATC | AAT | CAT | CCT | GTT | GAA | AAG | ATT | GCG | GAT | CGC | 1296 |
|---|---|---|---|---|---|---|---|---|---|---|---|---|---|---|---|---|
| Glu | Ile | Ser | Ser | Tyr | Ile | Asn | His | Pro | Val | Glu | Lys | Ile | Ala | Asp | Arg | |
| | | | 420 | | | | 425 | | | | | 430 | | | | |

| CAA | GAA | GCC | ATC | AAG | GCG | GCA | ATG | GCT | ATC | ACA | AAT | CAC | GAA | TTA | GAT | 1344 |
|---|---|---|---|---|---|---|---|---|---|---|---|---|---|---|---|---|
| Gln | Glu | Ala | Ile | Lys | Ala | Ala | Met | Ala | Ile | Thr | Asn | His | Glu | Leu | Asp | |
| | | 435 | | | | | 440 | | | | | 445 | | | | |

| GCA | GTT | ATT | ATT | GCG | GGT | AAG | GGA | GCC | GAT | TGT | TAC | CAA | ATC | ATC | CAG | 1392 |
|---|---|---|---|---|---|---|---|---|---|---|---|---|---|---|---|---|
| Ala | Val | Ile | Ile | Ala | Gly | Lys | Gly | Ala | Asp | Cys | Tyr | Gln | Ile | Ile | Gln | |
| | 450 | | | | | 455 | | | | 460 | | | | | | |

| GGC | AAG | AAA | GAA | TCC | TAC | CCA | GGA | GAT | ACA | GCC | GTC | GCA | GAA | AAT | TAT | 1440 |
|---|---|---|---|---|---|---|---|---|---|---|---|---|---|---|---|---|
| Gly | Lys | Lys | Glu | Ser | Tyr | Pro | Gly | Asp | Thr | Ala | Val | Ala | Glu | Asn | Tyr | |
| 465 | | | | | 470 | | | | | 475 | | | | | 480 | |

| TTA | TAA | | | | | | | | | | | | | | | 1446 |
|---|---|---|---|---|---|---|---|---|---|---|---|---|---|---|---|---|
| Leu | | | | | | | | | | | | | | | | |

( 2 ) INFORMATION FOR SEQ ID NO:2:

( i ) SEQUENCE CHARACTERISTICS:
        ( A ) LENGTH: 481 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ile | Lys | Ile | Glu | Thr | Val | Leu | Asp | Ile | Leu | Lys | Lys | Asp | Gly | Leu |
|---|---|---|---|---|---|---|---|---|---|---|---|---|---|---|---|
| 1 | | | | 5 | | | | | 10 | | | | | 15 | |

| Phe | Arg | Glu | Ile | Ile | Asp | Gln | Gly | His | Tyr | His | Tyr | Asn | Tyr | Ser | Lys |
|---|---|---|---|---|---|---|---|---|---|---|---|---|---|---|---|
| | | | | 20 | | | | | 25 | | | | | 30 | |

| Val | Ile | Phe | Asp | Ser | Ile | Ser | Tyr | Asp | Ser | Arg | Lys | Val | Thr | Glu | Asp |
|---|---|---|---|---|---|---|---|---|---|---|---|---|---|---|---|
| | | | 35 | | | | | 40 | | | | | 45 | | |

| Thr | Leu | Phe | Phe | Ala | Lys | Gly | Ala | Ala | Phe | Lys | Lys | Glu | Tyr | Leu | Leu |
|---|---|---|---|---|---|---|---|---|---|---|---|---|---|---|---|
| | 50 | | | | | 55 | | | | | 60 | | | | |

| Ser | Ala | Ile | Thr | Gln | Gly | Leu | Ala | Trp | Tyr | Val | Ala | Glu | Lys | Asp | Tyr |
|---|---|---|---|---|---|---|---|---|---|---|---|---|---|---|---|
| 65 | | | | | 70 | | | | | 75 | | | | | 80 |

| Glu | Val | Asp | Ile | Pro | Val | Ile | Ile | Val | Asn | Asp | Ile | Lys | Lys | Ala | Met |
|---|---|---|---|---|---|---|---|---|---|---|---|---|---|---|---|
| | | | | 85 | | | | | 90 | | | | | 95 | |

| Ser | Leu | Ile | Ala | Met | Glu | Phe | Tyr | Gly | Asn | Pro | Gln | Glu | Lys | Leu | Lys |
|---|---|---|---|---|---|---|---|---|---|---|---|---|---|---|---|
| | | | 100 | | | | | 105 | | | | | 110 | | |

| Leu | Leu | Ala | Phe | Thr | Gly | Thr | Lys | Gly | Lys | Thr | Thr | Ala | Thr | Tyr | Phe |
|---|---|---|---|---|---|---|---|---|---|---|---|---|---|---|---|
| | | | 115 | | | | | 120 | | | | | 125 | | |

| Ala | Tyr | Asn | Ile | Leu | Ser | Gln | Gly | His | Arg | Pro | Ala | Met | Leu | Ser | Thr |
|---|---|---|---|---|---|---|---|---|---|---|---|---|---|---|---|
| | | 130 | | | | | 135 | | | | | 140 | | | |

| Met | Asn | Thr | Thr | Leu | Asp | Gly | Glu | Thr | Phe | Phe | Lys | Ser | Ala | Leu | Thr |
|---|---|---|---|---|---|---|---|---|---|---|---|---|---|---|---|
| 145 | | | | | 150 | | | | | 155 | | | | | 160 |

| Thr | Pro | Glu | Ser | Ile | Asp | Leu | Phe | Asp | Met | Met | Asn | Gln | Ala | Val | Gln |
|---|---|---|---|---|---|---|---|---|---|---|---|---|---|---|---|
| | | | | 165 | | | | | 170 | | | | | 175 | |

| Asn | Asp | Arg | Thr | His | Leu | Ile | Met | Glu | Val | Ser | Ser | Gln | Ala | Tyr | Leu |
|---|---|---|---|---|---|---|---|---|---|---|---|---|---|---|---|

|                           |           180           |           185           |           190           |
|---|---|---|---|
| Val  His  Arg  Val  Tyr  Gly  Leu  Thr  Phe  Asp  Val  Gly  Val  Phe  Leu  Asn | | | |
|                195                |                200                |                205                | |
| Ile  Thr  Pro  Asp  His  Ile  Gly  Pro  Ile  Glu  His  Pro  Ser  Phe  Glu  Asp | | | |
| 210 | 215 | 220 | |
| Tyr  Phe  Tyr  His  Lys  Arg  Leu  Leu  Met  Glu  Asn  Ser  Arg  Ala  Val  Ile | | | |
| 225 | 230 | 235 | 240 |
| Ile  Asn  Ser  Asp  Met  Asp  His  Phe  Ser  Val  Leu  Lys  Glu  Gln  Val  Glu | | | |
|  | 245 | 250 | 255 |
| Asp  Gln  Asp  His  Asp  Phe  Tyr  Gly  Ser  Gln  Phe  Asp  Asn  Gln  Ile  Glu | | | |
|  | 260 | 265 | 270 |
| Asn  Ser  Lys  Ala  Phe  Ser  Phe  Ser  Ala  Thr  Gly  Lys  Leu  Ala  Gly  Asp | | | |
|  | 275 | 280 | 285 |
| Tyr  Asp  Ile  Gln  Leu  Ile  Gly  Asn  Phe  Asn  Gln  Glu  Asn  Ala  Val  Ala | | | |
|  | 290 | 295 | 300 |
| Ala  Gly  Leu  Ala  Cys  Leu  Arg  Leu  Gly  Ala  Ser  Leu  Glu  Asp  Ile  Lys | | | |
| 305 | | 310 | 315 | 320 |
| Lys  Gly  Ile  Ala  Ala  Thr  Arg  Val  Pro  Gly  Arg  Met  Glu  Val  Leu  Thr | | | |
|  | 325 | 330 | 335 |
| Gln  Lys  Asn  Gly  Ala  Lys  Val  Phe  Ile  Asp  Tyr  Ala  His  Asn  Gly  Asp | | | |
|  | 340 | 345 | 350 |
| Ser  Leu  Lys  Lys  Leu  Ile  Asn  Val  Val  Glu  Thr  His  Gln  Thr  Gly  Lys | | | |
|  | 355 | 360 | 365 |
| Ile  Ala  Leu  Val  Leu  Gly  Ser  Thr  Gly  Asn  Lys  Gly  Glu  Ser  Arg  Arg | | | |
|  | 370 | 375 | 380 |
| Lys  Asp  Phe  Gly  Leu  Leu  Leu  Asn  Gln  His  Pro  Glu  Ile  Gln  Val  Phe | | | |
| 385 | | 390 | 395 | 400 |
| Leu  Thr  Ala  Asp  Asp  Pro  Asn  Tyr  Glu  Asp  Pro  Met  Ala  Ile  Ala  Asp | | | |
|  | 405 | 410 | 415 |
| Glu  Ile  Ser  Ser  Tyr  Ile  Asn  His  Pro  Val  Glu  Lys  Ile  Ala  Asp  Arg | | | |
|  | 420 | 425 | 430 |
| Gln  Glu  Ala  Ile  Lys  Ala  Ala  Met  Ala  Ile  Thr  Asn  His  Glu  Leu  Asp | | | |
|  | 435 | 440 | 445 |
| Ala  Val  Ile  Ile  Ala  Gly  Lys  Gly  Ala  Asp  Cys  Tyr  Gln  Ile  Ile  Gln | | | |
|  | 450 | 455 | 460 |
| Gly  Lys  Lys  Glu  Ser  Tyr  Pro  Gly  Asp  Thr  Ala  Val  Ala  Glu  Asn  Tyr | | | |
| 465 | | 470 | 475 | 480 |
| Leu | | | |

( 2 ) INFORMATION FOR SEQ ID NO:3:

( i ) SEQUENCE CHARACTERISTICS:
        ( A ) LENGTH: 1446 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:3:

| AUGAUUAAGA | UUGAAACCGU | AUUAGAUAUU | UUAAAGAAAG | AUGGCCUUUU | UCGCGAAAUU | 60 |
|---|---|---|---|---|---|---|
| AUUGACCAAG | GUCAUUACCA | CUACAACUAC | AGCAAAGUUA | UUUUUGAUAG | CAUCAGCUAC | 120 |
| GACAGCCGAA | AAGUAACAGA | AGACACUCUU | UUUUUUGCAA | AAGGCGCUGC | CUUUAAAAAA | 180 |
| GAAUACCUUC | UUUCUGCUAU | AACACAAGGU | UUAGCUUGGU | AUGUAGCUGA | AAAGGACUAC | 240 |
| GAAGUCGAUA | UCCCUGUCAU | CAUUGUGAAC | GAUAUAAAGA | AAGCCAUGAG | UUUGAUUGCC | 300 |

| | | | | | | |
|---|---|---|---|---|---|---|
|AUGGAGUUCU|AUGGUAAUCC|ACAAGAGAAA|CUCAAACUCC|UUGCCUUUAC|UGGUACUAAG|360|
|GGUAAGACAA|CAGCAACCUA|UUUCGCCUAU|AACAUCUUAU|CUCAAGGGCA|UAGACCUGCU|420|
|AUGUUGUCGA|CCAUGAACAC|AACUCUUGAU|GGCGAGACUU|UCUUUAAGUC|AGCGUUGACA|480|
|ACCCCUGAGA|GUAUUGACCU|CUUUGACAUG|AUGAAUCAGG|CUGUGCAAAA|UGACCGUACC|540|
|CACCUCAUCA|UGGAAGUCUC|CAGUCAAGCC|UAUCUAGUCC|AUCGAGUCUA|UGGACUGACC|600|
|UUUGAUGUAG|GAGUCUUUCU|UAACAUCACU|CCUGACCAUA|UCGGCCCGAU|UGAACACCCU|660|
|AGCUUUGAAG|ACUAUUUCUA|CCACAAGCGU|CUCUUGAUGG|AAAAUAGCCG|AGCAGUCAUC|720|
|AUUAACAGUG|ACAUGGACCA|CUUCUCAGUC|UUGAAAGAAC|AGGUUGAAGA|UCAAGACCAU|780|
|GAUUUCUAUG|GUAGCCAAUU|UGAUAACCAA|AUCGAGAAUU|CCAAAGCCUU|UAGCUUUUCA|840|
|GCUACGGGUA|AACUCGCUGG|AGAUUAUGAU|AUCCAACUCA|UUGGCAACUU|CAACCAAGAA|900|
|AAUGCAGUUG|CUGCUGGACU|UGCUUGUCUC|CGUCUCGGAG|CAAGUCUUGA|GGACAUCAAA|960|
|AAAGGCAUCG|CUGCAACCCG|CGUUCCUGGU|CGUAUGGAAG|UCCUCACUCA|GAAAAAUGGA|1020|
|GCCAAGGUCU|UCAUCGACUA|UGCCCACAAU|GGGGAUAGUC|UGAAAAAACU|CAUCAAUGUG|1080|
|GUUGAAACUC|AUCAAACCGG|AAAGAUUGCU|CUGGUUCUGG|GAUCAACAGG|AAACAAGGGA|1140|
|GAAAGUCGUC|GUAAGGACUU|UGGCCUCCUC|CUCAAUCAAC|ACCCUGAGAU|UCAAGUCUUU|1200|
|CUGACUGCUG|AUGACCCUAA|CUAUGAAGAC|CCAAUGGCCA|UUGCAGAUGA|AAUUAGUAGC|1260|
|UACAUCAAUC|AUCCUGUUGA|AAAGAUUGCG|GAUCGCCAAG|AAGCCAUCAA|GGCGGCAAUG|1320|
|GCUAUCACAA|AUCACGAAUU|AGAUGCAGUU|AUUAUUGCGG|GUAAGGGAGC|CGAUUGUUAC|1380|
|CAAAUCAUCC|AGGGCAAGAA|AGAAUCCUAC|CCAGGAGAUA|CAGCCGUCGC|AGAAAAUUAU|1440|
|UAA| | | | | |1443|

We claim:

1. An isolated nucleic acid compound comprising a sequence encoding a MurE protein from *Streptococcus pneumoniae* or an enzymatically active fragment thereof wherein said compound has a sequence selected from the group consisting of a nucleic acid compound described in SEQ ID NO:1, SEQ ID NO: 3 and a nucleic acid compound complementary to SEQ ID NO:1 or SEQ ID NO:3.

2. An isolated nucleic acid compound of claim 1 wherein the sequence of said compound is SEQ ID NO:1 or a sequence complementary to SEQ ID NO:1.

3. An isolated nucleic acid compound of claim 1 wherein the sequence of said compound is SEQ ID NO:3 or a sequence complementary to SEQ ID NO:3.

4. A vector comprising an isolated nucleic acid compound of claim 1.

5. A vector, as in claim 4, wherein said isolated nucleic acid compound is DNA operably linked to a promoter sequence.

6. A host cell containing the vector of claim 4.

7. A host cell containing the vector of claim 5.

8. A method for constructing a recombinant host cell having the potential to express SEQ ID NO:2, said method comprising introducing into said host cell by any suitable means a vector of claim 5.

9. A method for expressing SEQ ID NO:2 in the recombinant host cell of claim 8, said method comprising culturing said recombinant host cell under conditions suitable for gene expression.

* * * * *